Figure 2:
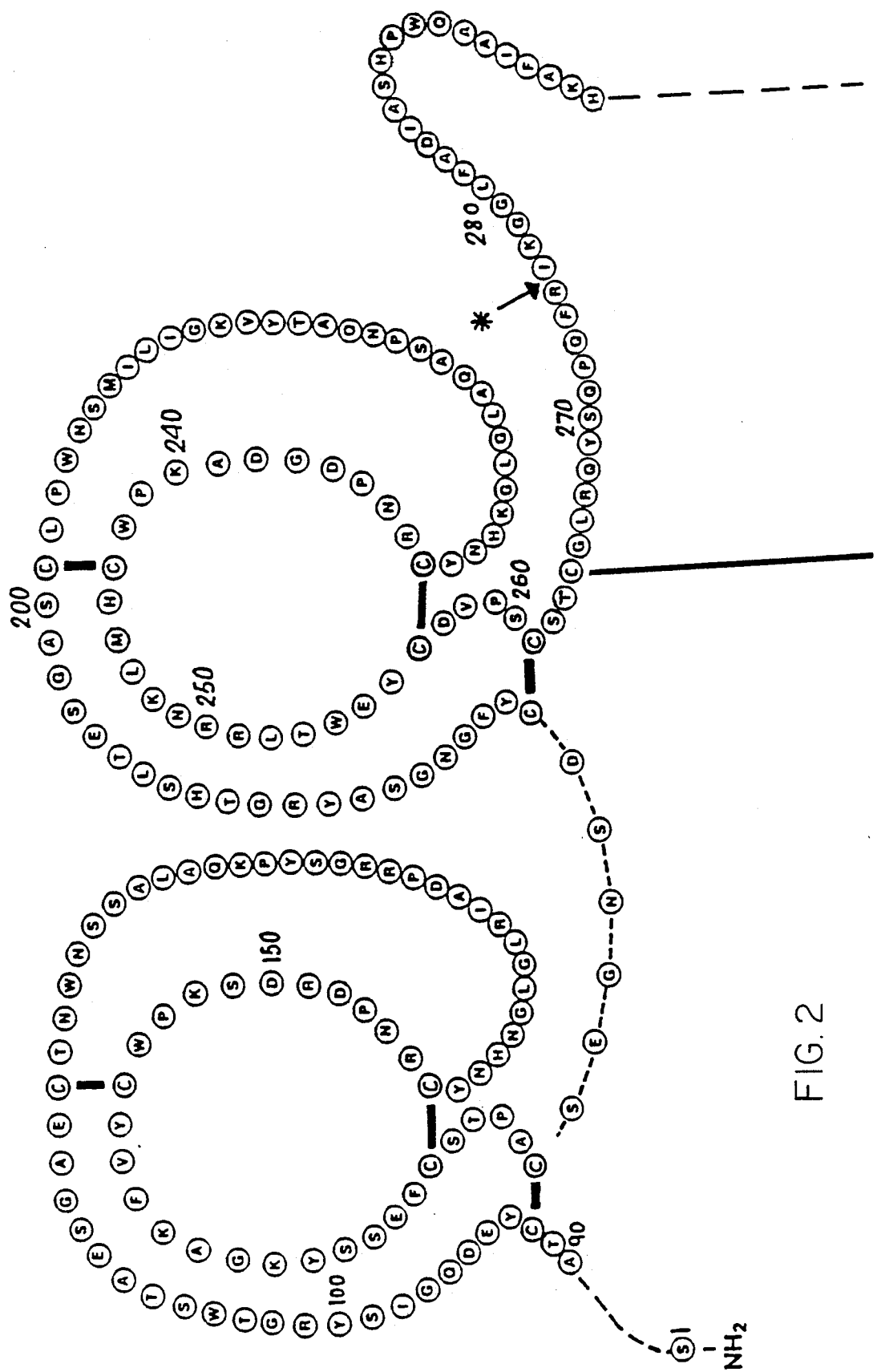
Figure 2A:
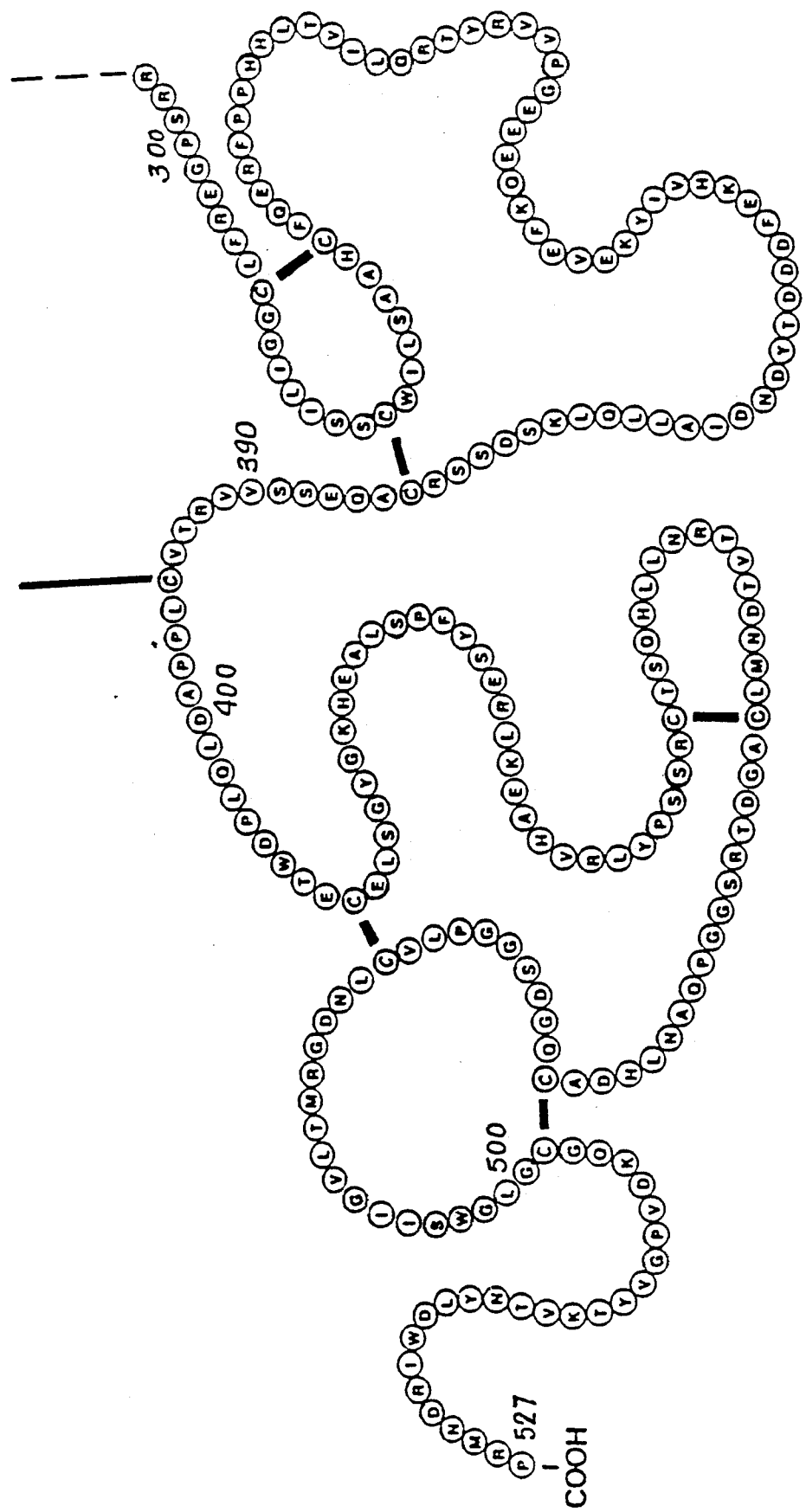

United States Patent [19]

Berger, Jr. et al.

[11] Patent Number: 4,976,959
[45] Date of Patent: Dec. 11, 1990

[54] T-PA AND SOD IN LIMITING TISSUE DAMAGE

[75] Inventors: Henry Berger, Jr., Cary; Crist J. Frangakis, Durham, both of N.C.

[73] Assignee: Burroughs Wellcome Co., Research Triange Park, N.C.

[21] Appl. No.: 862,057

[22] Filed: May 12, 1986

[51] Int. Cl.$^5$ .................. A61K 37/62; A61K 37/50; C12N 9/02; C12N 9/50

[52] U.S. Cl. .................. 424/94.2; 424/94.64; 424/94.4; 435/189; 435/212; 435/219

[58] Field of Search .................. 424/94.4, 94.2, 94.63; 435/189, 212, 219

[56] References Cited

U.S. PATENT DOCUMENTS

| | | | |
|---|---|---|---|
| 4,505,893 | 3/1985 | Mori et al. | 424/94.64 |
| 4,568,544 | 2/1986 | Hasegawa et al. | 424/94.1 |
| 4,656,034 | 4/1987 | Sarnoff | 424/94.4 |
| 4,661,469 | 4/1987 | Sarnoff | 424/94.4 |

FOREIGN PATENT DOCUMENTS

| | | |
|---|---|---|
| 0112122 | 6/1984 | European Pat. Off. |
| 0123304 | 10/1984 | European Pat. Off. |
| 2176702 | 1/1987 | United Kingdom. |
| 2176703 | 1/1987 | United Kingdom. |

OTHER PUBLICATIONS

Dalsing et al, cited in Chem. Abstracts vol. 99:51315h 1983.
Flameng et al, cited in Biol. Abstracts vol. 79(10) No. 88838 1985.
Werns et al, cited in Chem. Abstracts vol. 103:134760b 1985.
Steinman et al. J. Biol. Chem. 249(22) pp. 7326-7338 1974.
Jabusch et al Biochemistry 19, 2310-2316, 1980.
Barra et al FEBS Letters, vol. 120 No. 1 Oct. 1980 pp. 53-56.
Human enzymes, Radical Hunter, Emeryville, CA, Apr. 19, 1986, The Economist.
Darius et al, JACC, vol. 8, No. 1, Jul. 1986, pp. 125-131.
Central RD & MisBeckenham Chemical Information Group Enquiry Report, Title: Patent Search for Superoxide Dismutase.

*Primary Examiner*—Jacqueline Stone
*Attorney, Agent, or Firm*—Donald Brown

[57] ABSTRACT

A combination of t-PA and SOD of use in inhibiting damage to jeopardized tissue during reperfusion in a mammal.

13 Claims, 2 Drawing Sheets

Ser Tyr Gln Val Ile Cys Arg Asp Glu Lys Thr Gln Met Ile Tyr Gln Gln His Gln Ser
1
Trp Leu Arg Pro Val Leu Arg Ser Asn Arg Val Glu Tyr Cys Trp Cys Asn Ser Gly

Arg Ala Gln Cys His Ser Val Pro Val Lys Ser Cys Ser Glu Pro Arg Cys Phe Asn
50
Gly Gly Thr Cys Gln Gln Ala Leu Tyr Phe Ser Asp Phe Val Cys Gln Cys Pro Glu

Gly Phe Ala Gly Lys Cys Cys Glu Ile Asp Thr Arg Ala Thr Cys Tyr Glu Asp Gln

Gly Ile Ser Tyr Arg Gly Thr Trp Ser Thr Ala Glu Ser Gly Ala Glu Cys Thr Asn Trp
100
Asn Ser Ser Ala Leu Ala Gln Lys Pro Tyr Ser Gly Arg Arg Pro Asp Ala Ile Arg

Leu Gly Leu Gly Asn His Asn Tyr Cys Arg Asn Pro Asp Arg Asp Ser Lys Pro Trp
150
Cys Tyr Val Phe Lys Ala Gly Lys Tyr Ser Ser Glu Phe Cys Ser Thr Pro Ala Cys

Ser Glu Gly Asn Ser Asp Cys Tyr Phe Gly Asn Gly Ser Ala Tyr Arg Gly Thr His

Ser Leu Thr Glu Ser Gly Ala Ser Cys Leu Pro Trp Asn Ser Met Ile Leu Ile Gly Lys
200
Val Tyr Thr Ala Gln Asn Pro Ser Ala Gln Ala Leu Gly Leu Gly Lys His Asn Tyr

Cys Arg Asn Pro Asp Gly Asp Ala Lys Pro Trp Cys His Met Leu Lys Asn Arg Arg
250
Leu Thr Trp Glu Tyr Cys Asp Val Pro Ser Cys Ser Thr Cys Gly Leu Arg Gln Tyr

Ser Gln Pro Gln Phe Arg Ile Lys Gly Gly Leu Phe Ala Asp Ile Ala Ser His Pro Trp

Gln Ala Ala Ile Phe Ala Lys His Arg Arg Ser Pro Gly Glu Arg Phe Leu Cys Gly
300
Gly Ile Leu Ile Ser Ser Cys Trp Ile Leu Ser Ala Ala His Cys Phe Gln Glu Arg Phe

Pro Pro His His Leu Thr Val Ile Leu Gly Arg Thr Tyr Arg Val Val Pro Gly Glu Glu

Glu Gln Lys Phe Glu Val Glu Lys Tyr Ile Val His Lys Glu Phe Asp Asp Asp Thr
350
Tyr Asp Asn Asp Ile Ala Leu Leu Gln Leu Lys Ser Asp Ser Ser Arg Cys Ala Gln

Glu Ser Ser Val Val Arg Thr Val Cys Leu Pro Pro Ala Asp Leu Gln Leu Pro Asp
400
Trp Thr Glu Cys Glu Leu Ser Gly Tyr Gly Lys His Glu Ala Leu Ser Pro Phe Tyr

Ser Glu Arg Leu Lys Glu Ala His Val Arg Leu Tyr Pro Ser Ser Arg Cys Thr Ser

Gln His Leu Leu Asn Arg Thr Val Thr Asp Asn Met Leu Cys Ala Gly Asp Thr Arg
450
Ser Gly Gly Pro Gln Ala Asn Leu His Asp Ala Cys Gln Gly Asp Ser Gly Gly Pro

Leu Val Cys Leu Asn Asp Gly Arg Met Thr Leu Val Gly Ile Ile Ser Trp Gly Leu
500
Gly Cys Gly Gln Lys Asp Val Pro Gly Val Tyr Thr Lys Val Thr Asn Tyr Leu Asp

Trp Ile Arg Asp Asn Met Arg Pro
527

FIG. 1

T-PA AND SOD IN LIMITING TISSUE DAMAGE

The present invention relates to tissue plasminogen activator and superoxide dismutase, to pharmaceutical formulations containing them, and to their use in human and veterinary medicine.

It is believed that there is a dynamic equilibrium between the enzyme system capable of forming blood clots—the coagulation system—and the enzyme system capable of dissolving blood clots—the fibrinolytic system—which maintains an intact patent vascular bed. To limit loss of blood from injury, blood clots are formed in the injured vessels. After natural repair of the injury, the superfluous blood clots are dissolved through operation of the fibrinolytic system. Occasionally, blood clots form without traumatic injury and may lodge in major blood vessels resulting in a partial or even total obstruction to blood flow. When this occurs in the heart, lung or brain, the result may be a myocardial infarction, pulmonary embolism or stroke. These conditions combined are the leading cause of morbidity and mortality in the industrialised nations.

Blood clots consist of a fibrous network that is capable of dissolution by the proteolytic enzyme plasmin. The enzyme is derived from the inactive proenzyme, plasminogen, a component of blood plasma, by the action of a plasminogen activator. There are two immunologically distinct mammalian plasminogen activators. Intrinsic plasminogen activator, also known as urokinase, is an enzyme produced by the kidney and can be isolated from urine. It can also be prepared from a number of tissue culture sources. Extrinsic plasminogen activator, also known as vascular plasminogen activator and as tissue plasminogen activator (t-PA), can be isolated from many tissue homogenates (notably human uterus), the vascular cell wall and from some cell cultures. In addition to these two kinds of plasminogen activator, there is also a bacterial product, streptokinase, prepared from beta-haemolytic streptococci. A major drawback with both urokinase and streptokinase is that they are active throughout the circulation and not just at the site of a blood clot. They can, for example, destroy other blood proteins, such as fibrinogen, prothrombin, factor V and factor VIII so reducing blood clotting ability and increasing the risk of haemorrhage. In contrast, the biological activity of t-PA is dependent on the presence of fibrin to which it binds and where it is activated. Maximum activity is thus developed only at the site of a blood clot, i.e. in the presence of the fibrin network to be dissolved, and this greatly avoids the risk of haemorrahage.

The interruption of blood flow in a vessel generally leads to the onset of an ischaemic event. In this condition the tissue is deprived of oxygen and becomes jeopardized, a state in which the tissue is injured but still potentially viable. If however the condition is maintained for a period of, say, three or more hours, the tissue becomes necrotic and, once in this state, cannot be recovered. It is therefore important that reperfusion, i.e. the restoration of blood flow, takes place as soon as possible to salvage the tissue before it becomes permanently damaged. The problem though is that reperfusion itself, even if carried out before the tissue becomes necrotic, results in a complex group of phenomena, including the putative formation of the superoxide radical, that have a deleterious effect on hypoxic tissue. Consequently, reperfusion can lead only to the partial recovery of jeopardized tissue, the remainder being permanently damaged by the occurence of one or more of these phenomena.

It has now been found that a combination of t-PA and superoxide dismutase (SOD) inhibits the damage to jeopardized tissue during reperfusion by protecting it against one or more of the aforementioned phenomena. The mechanism of action of t-PA in affording such protection has not been elucidated but it is independent of its action as a thrombolytic agent. In contrast, SOD is an enzyme that is known to scavenge and destroy superoxide radicals, one of the phenomena capable of causing tissue damage. The combination of t-PA and SOD, however, has been found to provide a significantly potentiated level of inhibition compared with that provided by t-PA or SOD per se. Accordingly, the present invention provides a combination of t-PA and SOD.

The present invention affords a particularly convenient means both for the removal of blood clots and for the inhibition of damage to jeopardized tissue during subsequent reperfusion. Thus, the administration of t-PA and SOD will result first in the removal of the blood clot through the known thrombolytic action of t-PA and then in the ibhibition of tissue damage through the combined action of t-PA and SOD. Although the present invention may be used for the protection of any jeopardized tissue, it is particularly useful in inhibiting damage to jeopardized myocardial tissue.

The t-PA of use with the present invention may be any bioactive protein substantially corresponding to mammalian, and especially human, t-PA and includes forms with and without glycosylation. It may be one- or two-chain t-PA, or a mixture thereof, as described in EP-A-112 122 and, in the case of fully glycosylated human t-PA, has an apparent molecular weight on polyacrylamide gels of about 70,000 and an isoelectric point of between 7.5 and 8.0. Preferably the t-PA has a specific activity of about 500,000 IU/mg (International Units/mg, the International Unit being a unit of activity as defined by WHO, National Institute for Biological Standards and Control, Holly Hill, Hampstead, London, NW3 6RB, U.K.).

The amino acid sequence of t-PA preferably substantially corresponds to that set forth in FIG. 1. The sequence is thus identical to that in FIG. 1 or contains one or more amino acid deletions, substitutions, insertions, inversions or additions of allelic origin or otherwise, the resulting sequence having at least 80%, and preferably 90%, homology with the sequence in FIG. 1 and retaining essentially the same biological and immunological properties of the protein. In particular, the t-PA sequence is identical to that in FIG. 1 or has the same sequence but with the amino acid in the 245th position from the serine N-terminus being valine instead of methionine, either sequence optionally being without any of the first three amino acids or optionally having an additional polypeptide N-terminal presequence of Gly-Ala-Arg.

The amino acid sequence set forth in FIG. 1 has thirty-five cysteine residues and thus the potential for forming seventeen disulphide bridges. Based on analogy with other proteins whose structure has been determined in more detail, the postulated structure for the sequence (arising from disulphide bond formation) between the amino acid in the 90th position and the proline C-terminus is set forth in FIG. 2. The structure of the N-terminal region is less certain although some proposals have been put forward (*Progress in Fibrinolysis*, 1983, 6, 269–273; and *Proc. Natl. Acad. Sci.*, 1984, 81, 5355–5359). The most important features of the structure of t-PA are the two kringle regions (between the 92nd and the 173rd amino acids and between the 180th and 261st amino acids), which are responsible for the binding of the protein to fibrin, and the serine protease region, which comprises the major part of the B-chain and which is responsible for the activation of plasminogen. The amino acids of special significance in serine proteases are the catalytic triad, His/Asp/Ser. In t-PA these occur at the 322nd, the 371st and the 463rd positions. The disulphide bridge between the 264th and 395th cysteine amino acid residues is also important in that it holds together the A- and the B-chains in the two-chain form of t-PA.

In FIGS. 1 and 2, the conventional one and three letter codes have been employed for the amino acid residues as follows:

| Asp | D | Aspartic acid | Ile | I | Isoleucine |
|-----|---|---------------|-----|---|------------|
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptohan |
| Val | V | Valine | Gln | Q | Glutamine |
| Met | M | Methionine | Asn | N | Asparagine |

The t-PA may be obtained by any of the procedures described or known in the art. For example, it may be obtained from a normal or neoplastic cell line of the kind described in *Biochimica et Biophysica Acta*, 1979, 580, 140–153; EP-A-41 766 or EP-A-113 319. It is preferred, however, that t-PA is obtained from a cultured transformed or transfected cell line, derived using recombinant DNA technology as described in, for example, EP-A-93 619; EP-A-117 059 or EP-A-117 060. It is particularly preferred that Chinese hamster ovary (CHO) cells are used for the production of t-PA and are derived in the manner as described in *Molecular and Cellular Biology*, 1985, 5(7), 1750–1759. In this way, the cloned gene is cotransfected with the gene encoding dihydrofolate reductase (dhfr) into dhfr⁻CHO cells. Transformants expressing dhfr are selected on media lacking nucleosides and are exposed to increasing concentrations of methotrexate. The dhfr and t-PA genes are thus coamplified leading to a stable cell line capable of expressing high levels of t-PA.

The t-PA is, preferably, purified using any of the procedures described or known in the art, such as the procedures described in *Biochimica et Biophysica Acta*, 1979, 580, 140–153; *J. Biol. Chem.*, 1979, 254(6), 1998–2003; ibid, 1981, 256(13), 7035–7041; *Eur. J. Biochem.*, 1983, 132, 681–686; EP-A-41 766; EP-A-113 319 or GB-A-2 122 219.

The SOD of use with the present invention may be any bioactive protein substantially corresponding to any one or more of a group of enzymes known generally by this name. It is preferably of mammalian, and especially of bovine or human, origin and is generally associated with a metal cation by which it is normally classified. Examples of a metal cation include iron, manganese, copper and preferably combinations of copper with other metals, such as zinc, cadmium, cobalt or mercury, of which a copper/zinc combination is preferred. Both the manganese and the copper/zinc forms of SOD occur naturally in humans. The iron and manganese forms of SOD of bacterial origin both have a molecular weight of about 40,000 and are dimers. The manganese form of SOD of eukaryotic origin on the other hand has a molecular weight of about 80,000 and is a tetramer. The copper/zinc form of SOD of eukaryotic origin has a molecular weight of about 32,000 and is a dimer with one copper cation and one zinc cation per subunit. The copper cation is ligated to four histidine residues per subunit and the zinc cation is ligated between histidine and aspartic acid. There is also a copper/zinc form of SOD of eukaryotic origin which has a molecular weight of about 130,000 and which consists of four subunits. The molecular weights of the various forms of SOD were estimated using sedimentation equilibrium, molecular sieving or using polyacrylamide gels. The isoelectric points of the various forms of SOD range from 4 to 6.5 depending on the degree of sulphation and/or deamidation. Preferably, the specific activity of the copper/zinc form of SOD of bovine or human origin is at least 3000 U/mg (the unit of activity being as defined in *J. Biol. Chem.*, 1969, 244, 6049–6055).

The amino acid sequence of the copper/zinc form of SOD bovine or human origin preferably substantially corresponds to that set forth in *J. Biol. Chem.*, 1974, 249(22), 7326 to 7338, in the case of that of bovine origin, and *Biochemistry*, 1980, 19, 2310 to 2316 and *FEBS Letters*, 1980, 120, 53 to 55, in the case of that of human origin. The sequence is thus identical to that set forth in these articles or contains one or more amino acid deletions, substitutions, insertions, inversions or additions of allelic origin or otherwise, the resulting sequence having sufficient homology with the published sequence so as to retain essentially the same biological and immunological properties.

The amino acid sequence of the copper/zinc form of SOD of bovine origin contains three cysteine residues per subunit (*J. Biol. Chem.*, 1974, 249(22), 7326–7338). The intrachain disulphide bridge occurs between the Cys 55 and Cys 144 residues while the interchain disulphide bridge occurs between the Cys 6 residues. The amino acid sequence of the copper/zinc form of SOD of human origin contains four cysteine residues per subunit (*Biochemistry*, 1980, 19, 2310 to 2316 and *FEBS Letters*, 1980, 120, 53 to 55). The intrachain disulphide bridge occurs between the Cys 57 and Cys 146 residues while the interchain disulphide bridge occurs also between the Cys 6 residues. The Cys 111 residue remains free.

The SOD may be obtained by any suitable procedure described or known in the art. For example, it may be obtained from erythrocytes or from liver by an extraction procedure of the kind described in GB-A-1 407 807 and GB-A-1 529 890. Alternatively, SOD may be obtained from a cultured transformed or transfected cell line, derived using recombinant DNA technology as described in, for example, Australia patent application No. 27461/84 and EP-A -138 111.

The SOD is preferably purified using any suitable procedure described or known in the art, such as the procedure described in EP-A-112 299.

In using t-PA and SOD in the manner of the present invention, it is preferred to employ them in the form of a pharmaceutical formulation. Conveniently, t-PA and SOD may be presented together in a single formulation rather than using separate formulations for each protein. Accordingly, the present invention provides a pharmaceutical formulation, which comprises t-PA and SOD and a pharmaceutically acceptable carrier.

Generally, t-PA and SOD will be administered by the intravascular route and thus a parenteral formulation is required. It is preferred to present a lyophilised formulation to the physician or veterinarian because of the significant transportation and storage advantages that it affords. The physician or veterinarian may then reconstitute the lyophilised formulation in an appropriate amount of solvent as and when required.

Parenteral and lyophilised pharmaceutical formulations containing t-PA are known in the art. Examples of such art include EP-A-41 766, EP-A -93 619, EP-A-112 122, EP-A-113 319, EP-A-123, EP-A-113 319, EP-A-123 304, EP-A-143 081, EP-A-156 169, Japanese patent publication 57-120523 ( application No. 56-b 6936) and Japanese patent publication 58-65218 (Application no. 56-163145). Additional examples include UK patent applications Nos. 8513358, 8521704 and 8521705. All such formulations are also suitable for SOD and for the combination of t-PA and SOD.

Intravascular infusions are normally carried out with the parenteral solution contained within an infusion bag or bottle or within an electrically operated infusion syringe. The solution may be delivered from the infusion bag or bottle to the patient by gravity feed or by the use of an infusion pump. The use of gravity feed infusion systems does not afford sufficient control over the rate of administration of the parenteral solution and, therefore, the use of an infusion pump is preferred especially with solutions containing relatively high concentrations of t-PA. More preferred, however, is the use of an electrically operated infusion syringe which offers even greater control over the rate of administration.

The present invention also provides a method for inhibiting damage to jeopardized tissue during reperfusion in a mammal, which comprises administering to the mammal an effective amount of t-PA and of SOD. In the alternative, the present invention provides a combination of t-PA and SOD for use in human and veterinary medicine especially for use in inhibiting damage to jeopardized tissue during reperfusion in a mammal.

In using t-PA and SOD in the manner of the present invention, the proteins may be administered simultaneously or sequentially in separate formulations or may be administered simultaneously in a single formulation as described herein. If the proteins are administered sequentially, it is preferred that t-PA is administered first and SOD subsequently. In any event the delay in administering the second of the two proteins should not be such as to lose the benefit of a potentiated effect of the combination of the proteins in vivo in inhibiting tissue damage.

The present invention is particularly advantageous in inhibiting damage to jeopardized tissue arising from the occurence of a blood clot in that, as mentioned previously, both the removal of the blood clot and the protection of the jeopardized tissue can be achieved.

An effective amount of t-PA and SOD to inhibit damage to jeopardized tissue during reperfusion will of course depend upon a number of factors including, for example, the age and weight of the mammal, the precise condition requiring treatment and its severity, the route of administration, and will ultimately be at the discretion of the attendant physician or veterinarian. It is likely, however, that an effective amount, in the case of t-PA, will be in the range from 150,000 to 1,000,000 IU/kg bodyweight of patient per hour, and, in the case of SOD, will be in the range from 7,000 to 50,000 U/kg bodyweight of patient per hour, Thus, for a 70 kg adult human being, an effective amount per hour will generally be, in the case of t-PA, from 10,000,000 to 70,000,000 IU, and, in the case of SOD, from 500,000 to 3,500,000 U.

The following example is provided in illustration of the present invention and should not be construed in any way as constituting a limitation thereof.

EXAMPLE 1

Methodology

Male beagle dogs (10–12 kg) were anaesthetized with pentobarbital sodium, intubated, and ventilated with room air via a Harvard respirator. Catheters for infusion and arterial blood pressure measurement were implanted in the left jugular vein and left carotid artery. A thoracotomy was performed at the 4th intercostal space, the heart suspended in a pericardial cradle, and the left anterior descending artery (LAD) isolated just below the first major diagonal branch. An electromagnetic flow probe was placed on LAD. A 90 min occlusion of the LAD was produced by placing a snare of 1/0 silk suture distal to the flow probe. Treatment was initiated intravenously 15 min prior to release of the snare occlusion and continued for 45 min after release. The thoracotomy was closed, and the animals were allowed to recover from the surgical procedures. The animals were reanaesthetized 24 h after the occlusion, and the flow in the LAD reassessed. Then the heart was removed for postmortem quantification of infarct size.

Four groups of dogs were evaluated. Group I consisted of saline controls. Group II were administered 750,000 IU/kg t-PA, Group III were administered 16,500 U/kg bovine SOD, and Group IV were administered both 750,000 IU/kg t-PA and 16,500 U/kg bovine SOD. The formulations were all acidic saline solutions with a single formulation, containing both t-PA and SOD, being used for the Group IV animals.

Myocardial infarct size was quantified by an ex vivo dual perfusion technique. Cannulas were inserted into the LAD immediately distal to the site of occlusion and into the aorta above the coronary ostia. The LAD coronary bed was perfused with 1.5% triphenyl tetrazolium hydrochloride (TTC) in 0.02M potassium phosphate buffer, pH 7.4. The aorta was perfused in a retrograde manner with 0.5% Evans blue dye. Both regions were perfused with their respective stains at a constant pressure of 100 mm Hg for 5 min. The heart was cut into 8 mm slices perpendicular to the apex-base axis. The area of the left ventricle at risk of infarction due to its anatomical dependence on the LAD for blood flow was identified by the lack of Evans blue in this region. The region of infarcted myocardium within the area at risk was demarcated by the lack of staining of the tissue when perfused with TTC due to a loss of dehydrogenase enzymes.

Transverse ventricular sections were traced carefully onto clear acrylic overlays to provide a permanent record of infarct morphology and to allow planimetric confirmation of infarct size. Ventricular sections then were trimmed of right ventricular muscle, valvular, and fatty tissue. Total left ventricle, area at risk, and infarct were separated by careful dissection and weighed. Infarct size was expressed as percent of the anatomic area at risk. Statistical comparisons of the drug treatment groups to the control group were made using a one-way analysis of variance (ANOVA) using Bonferroni's method for multiple comparisons (*Circulation Research*, 1980, 47, 1–9). A P value of <0.05 was taken as the criterion of significance.

| GROUP | NUMBER OF DOGS | % AREA AT RISK* INFARCTED | % LEFT VENTRICLE* AT RISK |
|---|---|---|---|
| I. Saline | 5 | 35.0 ± 8.9 | 37.7 ± 7.6 |
| II. t-PA | 6 | 14.3 ± 11.7 | 35.7 ± 5.4 |
| III. SOD | 4 | 13.0 ± 4.6 | 30.6 ± 2.6 |
| IV. t-PA+ SOD | 3 | 2.3 ± 1.3 | 37.2 ± 9.1 |

*Data are expressed as means ± standard deviation.

The proportionm of the left ventricle made ischemic by mechanical occlusion of the LAD was not significantly different between the t-PA treatment group and the control group by ANOVA.

Conclusion

The use of t-PA and SOD significantly inhibited the myocardial infarct size thus demonstrating its ability to protect jeopardized tissue during reperfusion. The combination of t-PA and SOD achieved a synergistic effect in comparison to the levels of inhibition obtained with each of t-PA and SOD on its own.

Formulations

Formulations according to the present invention may be in the form of injectable solutions containing from 50,000 to 50,000,000 IU/ml of t-PA and 2,000 to 100,000 U/ml of SOD in saline solution (or other physiologically acceptable solution isotonic with the blood serum of the patient), preferably at a pH of 2.5 to 4.0, most preferably about 3.0. A lyophilized formulation comprising a mixture of t-PA and SOD in a ratio of about 3:1 to 120:1 may be conveniently prepared by lyophilizing a solution of t-PA and SOD in the desired ratio, said solution having a pH in the range of about 2 to 5, preferably about 3.0.

We claim:

1. A method for inhibiting damage to jeopardized tissue during reperfusion in a mammal, which comprises administering to said mammal an effective amount of t-PA in combination with an effective amount of SOD to provide a synergistic effect.

2. A method according to claim 1 wherein t-PA and SOD are administered concurrently.

3. A method according to claim 1, wherein t-PA and SOD are administered sequentially.

4. A method according to claim 3, wherein t-PA is administered first.

5. A method according to claim 1, wherein the mammal is a human being.

6. A method for inhibiting damage to jeopardized mycocardial tissue during reperfusion in a mammal, which comprises administering to said mammal an effective amount of t-PA and SOD, said t-PA and SOD being present in an amount to provide synergistic combination.

7. A method according to claim 6 wherein the mammal is a human being.

8. A composition comprising an amount of t-PA and an amount of SOD, the t-PA and SOD being present in an amount to provide a synergistic combination.

9. A combination according to claim 8, wherein the t-PA is either in the one-chain or in the two-chain form.

10. A combination according to claim 9, wherein the t-PA has the amino acid sequence set forth in FIG. 1 or has the same amino acid sequence but with the amino acid in the 245th position from the serine N-terminus being valine instead of methionine, either sequence optionally being without any of the first three amino acids or optionally having an additional polypeptide N-terminal presequence of Gly-Ala-Arg.

11. A combination according to claim 8, wherein the SOD is the copper/zinc form of bovine or human origin.

12. A pharmaceutical formulation, which comprises a synergistic combination of t-PA and SOD together with a pharmaceutically acceptable carrier.

13. A method of limiting the size of myocardial tissue damage in a mammal which has had an infarct and is being reperfused, said method comprises administering to said mammal in need thereof both t-PA and SOD in synergistic amounts to limit the amount of myocardial tissue damage during reperfusion.

* * * * *